(12) United States Patent
Ninkov

(10) Patent No.: US 6,322,825 B1
(45) Date of Patent: Nov. 27, 2001

(54) COMPOSITIONS CONTAINING THYMOL AND CARVACROL AND METHODS OF TREATING GASTROINTESTINAL INFECTIONS WITH THE COMPOSITIONS

(75) Inventor: Dusan Ninkov, Amstelveen (NL)

(73) Assignee: Ropapharm B.V., Zaandam (NL)

(*) Notice: Subject to any disclaimer, the term of this patent is extended or adjusted under 35 U.S.C. 154(b) by 0 days.

(21) Appl. No.: 09/356,499

(22) Filed: Jul. 19, 1999

Related U.S. Application Data

(63) Continuation of application No. 08/875,991, filed as application No. PCT/NL96/00210 on May 24, 1996, now abandoned.

(30) Foreign Application Priority Data

May 26, 1995 (MK) .................................... 950075
May 26, 1995 (MK) .................................... 950076

(51) Int. Cl.$^7$ ............................. A61K 35/78; C07C 39/06
(52) U.S. Cl. ........................ 424/745; 424/725; 424/747; 424/774; 568/781
(58) Field of Search ................ 424/195.1, 725, 424/745, 747, 774; 568/781

(56) References Cited

U.S. PATENT DOCUMENTS

| | | | |
|---|---|---|---|
| 3,939,260 | | 2/1976 | Lafon ..................................... 424/28 |
| 4,318,906 | * | 3/1982 | Llopart .............................. 424/195.1 |
| 5,142,817 | | 9/1992 | Rolf ........................................ 47/24 |
| 5,252,344 | | 10/1993 | Shi ........................................ 424/682 |
| 5,591,435 | * | 1/1997 | Vaccarello-Dunkel et al. .. 424/195.1 |
| 5,665,781 | * | 9/1997 | Warren et al. ....................... 514/703 |
| 6,106,838 | * | 8/2000 | Nitsas ................................ 424/195.1 |

FOREIGN PATENT DOCUMENTS

WO 97/01348    1/1997   (WO) .

OTHER PUBLICATIONS

Lawless, "The Illustrated Encyclopedia of Essential Oils: The Complete Guide to the Use of Oils in Aromatheraphy and Herbalism", Barnes & Noble Books, pp. 188, 227 and 228.

"Remington's Pharmaceutical Sciences", 16th Edition, pp. 1256–1267.
The Merck Index, 12th Edition, pp. 308 and 1604.
K.D. Gunther et al., "The Effect of Etheric Oil From Origanum Vulgaris (Ropadiar) in the Feed Ration of Weaned Pigs on Their Daily Need Intake, Daily Gains and Food Utilization", Oral Presentations, Jul. 5 to 9, 1998.
"Ropadiar Emulsion Clinical Examination Report", College of Veterinary Medicaine, China Agricultural University.
"Registered License for Animal Health Product", Apr. 1988.
D. Hoffman, The Herbal Handbook, A User's Guide to Medical Herbalism, Healing Arts Press, Rochester, Vt, p. 128, 1988.*
Guerin et al., Ann. Pharmaceutiques Francaises, 43:77–87, 1985.*
Lawless, The Illustrated Encyclopedia Of Essential Oils, The Complete Guide to the Use of Oils in Aromatheraphy and Herbalism, Element Books Inc., Rockport MA, pp. 141, 149, 175, and 212, 1995.*
The Merck Manual of Diagnosis and Theraphy, 16th Edition, Eds. Berkow, Fletcher, and Beers, Merck Research Laboratories, Merck & Co., Inc., Rahway, NJ, pp. 812–821, 1992.*

* cited by examiner

*Primary Examiner*—Christopher R. Tate
*Assistant Examiner*—Janet M. Kerr
(74) *Attorney, Agent, or Firm*—Young & Thompson

(57) ABSTRACT

The invention relates to pharmaceutical compounds which are based on the anti-flammatory properties of etheric oils selected from the group consisting of *Origanum vulgaris, Thymus vulgaris, Mentha piperita, Thymus serpilum, Saturea hortensis, Saturea montana, Saturea subricata, Carum corticum, Thymus zugis, Ocimum gratisimum, Moranda pungtata, Mosla japanoica* and *Salvia officinalis*. Preferably the etheric oils, obtained at the distillation of *Origanum vulgaris, Thymus vulgaris* and/or *Mentha piperita* are used. Such pharmaceutical compounds, compared to synthetic sulfonamids, antibiotics and cortisones do not create biorecidives in the human body as well as in animal meat and milk and milk and do not contribute to the resistance of microorganism against pharmaceutical compositions in general. The composition according to the invention can be used in the treatment of colibacillosis, dermatomycosis, lice, perspiration and fungas on feet, dermatitis, acne and of veterinary diseases such as coccidiosis and mastitis.

10 Claims, No Drawings

COMPOSITIONS CONTAINING THYMOL AND CARVACROL AND METHODS OF TREATING GASTROINTESTINAL INFECTIONS WITH THE COMPOSITIONS

CROSS-REFERENCE TO RELATED APPLICATIONS

This application is a continuation of application Ser. No. 08/875,991 filed Jan. 26, 1998 abandoned, which is a 371 of PCT/NL96/00210 filed May 26, 1996.

DESCRIPTION

1. Field of Technology

The invention relates to pharmaceutical compositions, comprising etheric oils extracted from specific plants, a process for preparing such pharmaceutical compositions, as well as to the application of said compositions in the human and veterinary medical field.

2. Technical Problems Solved With This Invention

One of the technical problems that is solved with this invention is the utilization of various types of human medicaments on the basis of active natural components that successfully replace prior art medicaments based on sulfonamids, antibiotics, cortisones etc., whereby the new products according to the invention:

1. do not create biorecidives in the human body;
2. do not generate resistance of microorganisms;
3. are ecologically unsuspected; and
4. are not toxic, mutagenic or teratogenic.

Another problem that is solved with this invention is the utilization of various types of veterinary medicaments on the basis of natural components, that successfully replace prior art products based on sulfonamids, antibiotics etc.. The application of the active substances according to the invention eliminates many unwanted effects caused by the prior art products like sulfonmaids and antibiotics, such as:

1. the presence of biorecidives in the meat and milk of animals treated with such products; and
2. the resistance of microorganisms-bacteria against the prior art products.

DESCRIPTION OF THE PRIOR ART

In the prior art known medicaments for curing human diseases like: cholera, colibacillosis, dermatomycosis, inflammation of the oral mucosa and pharynx, fungicidal and bacteriological infections, inflammation of the mucous membrane of the vagina, colitis, various etiologies, the treatment of festered wounds, are based on active substances that have an antibiotic, sulfonmaid or hormonal corticoidal origin.

The tendencies of modern science are to substitute a part of the medicaments based on such origins by ecologically healthy drugs, which are much easier for the human organism to bear and have a much more beneficial influence on human health.

The same counts for veterinary medicaments based on antibiotics, sulfonamids and even hormones for treating animal diseases such as cholera, different types of colibacillosis, dermatomycosis, inflammation of the udder, inflammation of the vagina and uterus, various etiologies and coccidiosis. In order to avoid the unwanted consequences mentioned above, it is necessary to have ecologically healthy and unsuspected products for treating these veterinary diseases.

More in particular a great deal of the bacteria that cause the abovementioned diseases have developed a form of resistance against the prior art medicaments, so the products according to the invention resolve the problems of treating the diseases listed above, as well as various types of diarrhea, inflammation of the abdomen, gastritis, inflammation of the oral mucosa, inflammation of the ear, conjunctivitis, etc.

DESCRIPTION OF THE SOLUTION TO THE ABOVE-DESCRIBED PROBLEM

The primary component which is applied in the pharmaceutical compositions according to the invention is etheric oil obtained from any of the following plants: *Origanum vulgaris, Thymus vulgaris, Mentha piperita, Thymus serpilum, Saturea hortensis, Saturea montana, Saturea subricata, Carum corticum, Thymus zugis, Ocimum gratisimu, Moranda pungtata, Mosla japonoica* and *Salvia officinalis*. Preferably the etheric oil is obtained from any of the following plants: *Origanum vulgaris, Thymus vulgaris* and *Mentha piperita*. Most preferably the etheric oil is at least obtained from *Origanum vulgaris* and optionally from *Thymus vulgaris*.

In case of veterinary medicaments it is also possible to use synthetic thymol having the chemical name isopropylcresol. Further the compound tannin may be used in veterinary compositions. This tannin can be recovered by extracting the residue of the leaves and blossoms of the *Origanum vulgaris* plants obtained after the etheric oil-distillation (see below).

The pharmaceutical compositions according to the invention may comprise a pharmaceutically acceptable carrier, preferably of natural origin. Representatives of such carriers are generally known in the human and veterinary pharmaceutical field. Examples of such carriers are lactose, honey, laurel, vaseline, paraffin, starch products, calcium carbonate, etc.

The pharmaceutical compositions may have any form suitable for its application, for instance the form of a capsule, syrup, tincture, ointment, powder, emulsion, paste, etc.

The content of active agent in the pharmaceutical compositions according to the invention, which in fact does also depend on its pharmaceutical use, may vary between wide limits. Preferably the active agent is present in an amount of 1–15% by weight, most preferably 4–10% by weight, calculated on the total weight of the pharmaceutical composition.

In addition to the active agent according to the invention also other active substances, preferably of natural origin, can be used. Such substances may have bacteriological, fungicidal, adstrigidic etc, properties.

The following dosage of a pharmaceutical composition, comprising 5% by weight of oil free *Origano vulgaris* and 95% by weight of calcium carbonate in powder form may be applied for mass and individual treatment:

A) Mass treatment:
  Preventive dose;
  pigs, rabbits, calves:
    500 g of powder per ton of feed
  chickens, ducks, turkeys:
    450 g of powder per ton of feed
  Therapeutical dose:
  pigs, rabbits, calves:
    1000 g of powder per ton of feed
  chickens, ducks turkeys:

900 g of powder per ton of feed for 7–10 days of therapy.

B) Individual treatment:
calves, foals:
0.20–0.25 g per kg of body weight
piglets, lambs, kids:
0.10 g per kg of body weight For illustrating the pharmacetucial activity of etheric oil from *Origanum vulgaris* (origanum oil) the following "antibiogram" of origanum oil is illustrated in Table A:

TABLE A

| Microorganisms | Intensity of Effect |
| --- | --- |
| Staphylococcus aureus | +++ |
| Treponema hyodisaenteriae | ++++ |
| Erysipelothrix insidiosa | +++ |
| Pasteurella multocida | ++++ |
| Streptococcus faecalis | +++ |
| Streptococcus agalactiae | +++ |
| Proteus mirabilis | +++ |
| Proteus vulgaris | +++ |
| Proteus rettgeri | +++ |
| Escherichia coli | ++++ |
| Vibrio coli | ++++ |
| Salmonella spp. | ++++ |
| Streptococcus pyogenes anim.C | +++ |
| Klebsiella pneumoniae | +++ |
| Enterobacter aerogenes | +++ |
| Corynebacterium pyogenes | +++ |
| Streptococcus uberis | +++ |
| Candida spp. | +++ |
| Pseudomonas aeruginosa | +++ |
| Mycobacterium tuberculosis | ++++ |
| Aspergilus spp. | ++++ |
| Mucor spp. | +++ |
| Cryptosporidiae spp | ++++ |
| Eimeria spp. (coccidiosis) | ++++ |

0 resistant;
+ relatively sensitive;
++ moderately sensitive;
+++ very sensitive;
++++ extremely sensitive.

In view of the data in the above Table A it is stated that diseases, caused by the microorganisms in Table A can be cured by pharmaceutical preparations based on origanum oil as active component.

In view of the above, the pharmaceutical compositions are particularly used for prevention and treatment of gastrointestinal infections in humans and particularly in animals, which are caused by the bacteria, fungi etc.; see in this respect the enumeration below:

Pigs: *E. Coli*, Salmonella spp., swine dysentery, Pasteurella spp.

Poultry: (chickens, ducks turkeys): Eimeria spp. (coccidiosis), Salmonella spp., Pasteurella spp.

Rabbits: Eimeria spp. (coccidiosis), Salmonella spp.

Cows: calves-*E. coli*, Pasteurella spp., Salmonella spp.

Lambs: Salmonella spp., Pasteurella spp., *Clostridium perfrigens, E. coli.*

Young goats: (kids): Salmonella spp., Paasteurella spp., Clostridium spp., *E. coli.*

Further to the diseases mentioned above, the pharmaceutical composition according to the invention can be applied for the treatment of:

toxoplasmosis cause by *Toxoplasma gondii* by animals and humans;

internal paristies of dogs like *Toxocara canis, Echinococcus granulosis* etc.:

sarcocystoses by dogs, cattle, poultry and humans;

ascaridosis by pigs and poultry, cause by *Ascaris suum* and *Ascaris golii;* oxyurosis equi by horses and heteracidosis by poultry;

teniosos by humans and cysticerocis by pigs;

ancylostoma duodenalis and oxyurosis by humans;

rheumatic diseases like arthritis, spondilitis, dyscioathie, and injuring like distorsio, subluxatio etc.;

fungi and insects on plants in the agricultural sector;

demodicosis by dogs;

diarrhea, caused by *Escherichia coli* (*colibacillosos*). Salmonella spp. (*salmonellosis*), Pasteurella spp. (*pasteurellosis*), Streptococcus spp. (*streptococcosis*), Vibrio coli (*vibrisis*). *Treponema hyodesynterie* (dysentery-bloody diarrhea), and other kinds of diarrhea by human and animals;

parasitosis caused by Cryptosporidia spp., Ascaridia spp., Toxocara spp., Toxoplasma spp., Atoxoplasmosa;

diseases caused by *Canida albicans,* Aspergilus spp., *Crypotococcus neoformans,* Mucor spp., Fusarium spp., by humans and animals; and cestodosis by birds and poultry.

The compositions according to the invention, in particular in the form of a powder comprising 5% of origanum vulgare oil, can also be used for the conservation of food for humans and for the conservation of feed for animals and prolongs the storage life of such products.

A process for extracting the etheric oils from the above-mentioned plants, in particular *Origanum vulgaris, Thymus vulgaris* and *Mantha piperita* is carried out by distillation with the help of water vapour (steam).

Firstly, the leaves and blossoms of the plants, which must be dry, are placed in a distiller. In case of human application of the oils obtained, the distillation of the oil from every type of plants is done separately, which means that different types of plants must not be mixed together in the process of distillation.

The distiller should have two output tubes: one for the oil and one for the water vapour (steam). The dish for the water is placed under the dry parts of the plant (the leaves and blossoms) and heated up to 100° C., preferably under a pressure of about 20 bar as an increased pressure will reduce the distillation time. The water vapour passes through the dry parts of the plant, thereby creating oil drops. The drops of water vapour are lighter than the oil drops, hence flow out the output tube at the bottom of the extractor. The drops of oil flow out the output tube for the oil and into the dish intended for the oil. This process is carried out for 3 hours. The yield is 3–6 kg of oil from 100 kg of dry plants. In general the extracted oil contains a certain percentage of thymol and carvacrol: approx. 3% of thymol and 60–70% of carvacrol.

After the above-described distillation, the residue of the leaves and blossoms is used to extract tannin, which can be added to, in particular, veterinary pharmaceutical compositions.

More in particular the procedure for obtaining etheric oils from *Origanum vulgaris* plants consists of four phases:

Phase 1: Selection

On the basis of the existing types of *Origanum vulgaris* plants it has been possible to obtain seeds of *Origanum vulgaris* plants having about 91% active material: 86–88% carvacrol and 3–5% thymol. The remaining 8–10% comprises the following components: linalol, barneol, cimen and some other less important components.

Phase 2: Production of the plants

The seeds obtained in the way according to phase 1 are planted in fine loose soil, preferably in a sub-tropical climate. During this process all agro-technical measure are applied, like watering and artificial fertilizing.

From the already grown plants, only their leaves and blossoms should be used. The reaping should be undertaken while the plants are in blossom early in the morning or late in the evening hours.

Phase 3: Drying of the leaves and blossoms

The drying process is performed in special rooms, i.e. drying houses. The already harvested leaves and blossoms should not be exposed to direct sunlight since any exposure to sunlight significantly decreases the percentage of active material.

The leaves and blossoms are arranged in layers of 20–25 cm thick. During the first three days, these layers should be turned up-side-down four times a day, either manually or mechanically, so that this drying process is proceeded in an uniform way.

These drying houses are constructed in such a way, that the air is able to circulate freely all the time.

The drying process lasts about 7–8 days.

Phase 4: Production of the oil

From the dried leaves and blossoms of the plants, a distillation of the oil is carried out on the basis of a classic steam distillation. Out of 100 kilos of dried leaves and blossoms 5–7 kilos of oil are obtained.

After the distillation step according to which the oil has been obtained, the following step is carried out:

the oil is heated at 187° C., during which process, again performed in the distillator, the substances, which are of no importance are evaporated. The remnants are the important substances: carvacrol 86–88%; thymol 3–5% and in minor quantities: pinene, barneol, linalol etc.

After this redistillation process, the oil is left to cool to room temperature and is then packed in hermetically closed vessels made of aluminum or dark glass.

The invention will be elucidated by the following series of examples, i.e. (A) examples concerning the compositions and preparation of human pharmaceutical medicaments, (B) examples concerning the compositions and preparation of veterinary pharmaceutical medicaments. (C) examples concerning the activity of pharmaceutical medicaments according to the invention and (D) examples concerning the safety of pharmaceutical medicaments according to the invention. The percentage is expressed as percentage by weight unless otherwise indicated.

A) COMPOSITION AND PREPARATION OF HUMAN PHARMACEUTICAL MEDICAMENTS

EXAMPLE 1

Medicaments for the treatment of colibacillosis, salmonellosis, pasteurellosis, vibriosis and cholera: the diseases are caused by *Escherichia coli, Salmonella typhimuxium, Vibrio fetus* and *Pasteurella multocida.*

1.1 Procedure for making capsules.

The integral parts of the substances from which the medicament is prepared are:

| | |
|---|---|
| lactose | 90–92% |
| *Origanum vulgaris* oil | 4–6% |
| *Thymus vulgaris* oil | 2–4% |
| *Mentha piperita* oil | 0.5–1.5% |

Firstly, about 30% of the lactose and the total amount of oils are put in a vacuum mixer. The mixture is mixed for five minutes at a speed of 200 rotations per minute. Then the rest of the lactose is added and everything is mixed together for another 10 minutes at the above-mentioned speed. Finally, the powder is packed into capsules.

1.2 Procedure for making a syrup.

The integral parts of the substances from which the medicament is prepared are:

| | |
|---|---|
| honey as the basic element | 92–94% |
| *Origanum vulgaris* oil | 2–4% |
| *Thymus vulgaris* oil | 1–3% |
| *Mentha piperita* oil | 0.5–1.5% |

30% of the overall amount of honey in a liquid form is placed in a vacuum mixer and the whole amount of oils is added. The mixture is mixed for 15 minutes at a speed of 200 rotations per minute. Then the rest of the honey is added and mixed for another 15 minutes at the above-mentioned speed. The resulting product is a syrup in liquid form, which can be packed as soon as it is cooled down.

EXAMPLE 2

Medicaments for the treatment of dermatomycosis: dermatomycosis may be caused by Trychophiton sp. and Microspora sp.

2.1 Process for obtaining a tincture.

The integral parts of the substances used to prepare the medicament are:

| | |
|---|---|
| polyethylene glycol | 72–74% |
| laurel | 19–21% |
| *Origanum vulgaris* oil | 3–5% |
| *Thysus vulgaris* oil | 1–3% |
| *Mentha piperita* oil | 0.5–1.5% |

Approximately 30% of the overall amount of polyethylene glycol is heated in a vacuum mixer up to 55° C. The total quanity of oils is added and mixed at a speed of 200 rotations per minute. At the end the rest of the polyethylene glycol and the laurel are added and this is mixed for five more minutes at the above-mentioned speed. After it is cooled down, the product is ready to be packed.

2.2 Procedure for making an ointment.

The integral parts of the substances used to make the ointment are:

| | |
|---|---|
| vaselin album | 67–69% |
| parafinum liquidum | 24–26% |
| *Origanum vulgaris* oil | 3–5% |

| | |
|---|---|
| *Thymus vulgaris* oil | 1–3% |
| *Mentha piperita* oil | 0.5–1.5% |

30% of the vaseline album is melted in a vacuum mixer at a temperature of 45° C. The oils are added and everything is mixed together for 10 minutes at a speed of 250 rotations per minute. Then, the rest of the vaselin and the parafinum liquidum are added. Everything is mixed for another 10 minutes at the above-mentioned temperature and packed after it is cooled down.

EXAMPLE 3

Medicaments for the treatment of colpitus (for women): colpitus may be caused by *Trychomonos genetalis*.

The substances used to prepare this medicament are:

| | |
|---|---|
| starch dextrose | 51–53% |
| hygroscopic carrier | 19–21% |
| kolloid | 19–21% |
| *Origanum vulgaris* oil | 2–4% |
| *Thymus vulgaris* oil | 2–14% |
| Klamath weed oil | 1–3% |

The process is as follows: the starch dextrose and the neutral hygroscopic carrier are placed in a vacuum mixer. The prescribed quantities of oils are added to this mixture and everything is blended at a speed of 200 rotations per minute. At the end, the kolloid is added, everything is mixed once more, and packed.

EXAMPLE 4

Repellent for lice and other types of skin insects: e.g. mosquitos and flies.

The substances used to obtain the product are:

| | |
|---|---|
| Laurel | 91–93% |
| *Origanum vulgaris* oil | 4–6% |
| *Thymus vulgaris* oil | 2–4% |

All the components listed above are put in a vacuum mixer. They are mixed together at a speed of 200 rotations per minute, for 10 minutes, after which the mixture is packed. The advantage of this product over the chemical varieties based on lindane is that the medicaments according to the invention are completely non-toxic for humans and animals.

EXAMPLE 5

Product for the prevention of foot perspiration and of the presence of fungus on feet: Trychophiton sp. and Microspora sp.

The substances that are used in the procedure for preparing these medicaments are:

| | |
|---|---|
| calcium carbonate | 91–93% |
| *Origanum vulgaris* oil | 4–6% |
| *Thymus vulgaris* oil | 2–4% |

30% of the calcium carbonate and the total amount of the oils are put in a vacuum mixer. The mixture is mixed for 10 minutes at a speed of 200 rotations per minute and subsequently the rest of the calcium carbonate is added. The mixing is continued until a powder is obtained.

EXAMPLE 6

Product for the extermination of insects and other pest: e.g. mosquitos and flies.

The substances that are used in the process of preparing this product are:

| | |
|---|---|
| calcium carbonate | 91–93% |
| *Origanum vulgaris* oil | 4–6% |
| *Thymus vulgaris* oil | 2–4% |

30% of the calcium carbonate together with the entire amount of oil is put in a vacuum mixer. The mixture is blended for 10 minutes at a speed of 200 rotations per minute. Subsequently, the rest of the calcium carbonate is added and the mixing is continued until a fine powder is obtained.

EXAMPLE 7

Medicament for the treatment of dermatitis, acne and other inflammations of the skin on the face.

The substances from which the medicament are prepared are:

| | |
|---|---|
| laurel | 72–74% |
| ethanol | 19–21% |
| *Origanum vulgaris* oil | 3–3% |
| *Thymus vulgaris* oil | 2–4% |

Some 30% of the laurel together with the whole amount of oils is put in the vacuum mixer. It is mixed for 10 minutes at a speed of 200 rotations per minute. Subsequently, the rest of the laurel and the ethanol are added and the product is mixed and packed in dark glass bottles.

EXAMPLE 8

Medicament for Wounds

The substances used in the process for preparing the medicament are:

| | |
|---|---|
| neutral medical powder | 94–96% |
| *Origanum vulargis* oil | 2–4% |
| *Thymus vulgaris* oil | 1–3% |

30% of the neutral medical powder and the total amount of oils are put in the vacuum mixer and mixed together for 10 minutes at a speed of 200 rotations per minute. Subsequently, the rest of the neutral medical powder is added and mixed. The product is packed in small bags or aluminum tubes under pressure.

COMPOSITIONS AND PREPARATION OF VETERINARY PHARMACEUTICAL MEDICAMENTS

EXAMPLE 9

Medicaments for the treatment of colibacillosos and gastroenteric diseases in animals: colibacillosis may be caused by *Escherichia coli* and other species: Salmonella, Pasteurella, Vibrio, Treponema, Hiodysenterie and Cryptosporidiosae sp.

9.1 Procedure for making a powder.

The substances which are used in the procedure for making a powder for the treatment of colibacillosis are:

| calcium carbonate | 91–93% |
|---|---|
| *Origanum vulgaris* oil | 3–5% |
| *Thymus vulgaris* oil | 1–3% |
| *Mentha piperita* oil | 0.5–1.5% |
| tannin | 0.5–1.5% |

30% of the total quantity of calcium carbonate is put in a turbo vacuum mixer and the entire amount of etheric oils is gradually added. The total product is mixed together at a speed of 250 rotations per minute for 10 minutes. The etheric oils are mixed together directly before being poured in the mixer. After the mixing time of 10 minutes, the rest of the calcium carbonate is added and mixed at the above-mentioned speed for another 5 minutes. The powder is then ready to be packed.

9.2 Procedure for making an emulsion.

In one case the substances which are used in the procedure for preparing the product are:

| polyethylene glycol | 89.5–91.5% |
|---|---|
| *Origanum vulgaris* oil | 3–5% |
| *Thymus vulgaris* oil | 1–3% |
| *Mentha piperita* oil | 0.5–1.5% |
| tannin | 0.5–1.5% |
| glycerol monostearate | 1–2% | and in the second case these substances are:

| laurel oil | 91–93% |
|---|---|
| *Origanum vulgaris* oil | 3–5% |
| *Thymus vulgaris* oil | 1–3% |
| *Mentha piperita* oil | 0.5–1.5% |
| tannin | 0.5–1.5% |

The procedure is in both cases the same. Firstly, 30% of the basic substance is placed in a turbo vacuum mixer (in the first case, the polyethylene glycol, and in the second case the laurel oil) and the mixture of oils is added. Everything is mixed together for a period of 5 minutes at a speed of 200 rotations per minute. After this is done, the rest of the basic substance is added. In the first case the glycerol monostearate is added as well. It is mixed for another 10 minutes with the same intensity. At the end it is packed in dark glass bottles.

9.3 Procedure for the production of capsules.

The substances which are used in the procedure for preparing the product are:

| lactose | 91–93% |
|---|---|
| *Origanum vulgaris* oil | 3–5% |
| *Thymus vulgaris* oil | 1–3% |
| *Mentha piperita* oil | 0.5–1.5% |
| tannin | 0.5–1.5% |

Firstly, the three types of oils are mixed in the given percentage. The mixture is then blended together in a mixer with 30% of the lactose at a speed of 200 rotations per minute for a period of 10 minutes. The rest of the lactose is added and mixed again. The mixture is then put in capsules.

9.4 Procedure for making a paste.

The elements which are used in the procedure are:

| vaselinum album | 69–71% |
|---|---|
| *Origanum vulgaris* oil | 3–5% |
| *Thymus vulgaris* oil | 1–3% |
| *Mentha piperita* oil | 0.5–1.5% |
| tannin | 0.5–1.5% |
| parafinum liquidum | 21–23% |

The procedure for making the paste goes as follows: the vaselinum album is placed in the mixer together with 20% of the total contents and heated up to a temperature of 40° C. The heated mass is then added to the mixture of above-mentioned quantities of oil and the product is mixed together for 5 minutes at a speed of 100 rotations per minute. At the end the parafinum liquidum is added and the product is packed.

EXAMPLE 10

Product for the Treatment and Prevention of Coccidiosis in Livestock

Coccidiosis may be caused by *Eimeria tenella, Eimeria phasani, Eimeria mecarriz, Eimeria duodenalis, Eimeria acervulina, Eimeria colchici, Eimeria maxima, Eimeria praecox, Eimeria brunetti, Eimeria Hagani, Eimeria mitis, Eimeria mivoti.*

The substances which are used in the preparation of the product are:

| calcium carbonate | 92–94% |
|---|---|
| *Origanum vulgaris* oil | 3–5% |
| *Thymus vulgaris* oil | 1–3% |
| *Menths piperita* oil | 0.5–1.5% |

20% of the calcium carbonate is put in a turbo vacuum mixer and the total amount of oils is added after being mixed beforehand. The product is blended together for 10 minutes at 200 rotations per minute. Then the rest of the calcium carbonate is added and mixed again for another 10 minutes. Finally the product is packed.

EXAMPLE 11

Product for the Treatment of Mastitis

Mastitis may be caused by *Streptococcus uberis, Staphilococcus aureus, Escherichia coli, Cryptococcus neoformans, Candida albicans, Spheroforus necroforus, Streptococcus agalactie.*

The substances which are used in the procedure for the preparation of the product are:

| | |
|---|---|
| vaselinum album | 92–94% |
| Parafinum liquidum | 22–24% |
| Origanum vulgaris oil | 3–5% |
| Mentha piperita oil | 0.5–1.5% |

20% of the vaselinum album is put in a mixer that is previously heated at 45° C. After the substance is melted the mixture of the given quantities of oils is added and mixed for 5 minutes at a speed of 200 rotations per minute. The rest of the vaselinum album and all of the parafinum liquidum are added as the product tools down. Then, the product is packed in appropriate syringes.

EXAMPLE 12

Product Having Anti-Dermatitis Properties

Dermatitis can be caused by Trychophiron sp. and Microspora sp.

The substances used in the procedure for preparing the product are:

| | |
|---|---|
| vaselinum album | 69–71% |
| parafinum liquidum | 21–23% |
| Origarium vulgaris oil | 3–5% |
| Thymus vulgeris oil | 2–4% |
| Mentha piperita oil | 0.5–1.5% |

20% of the vaselinum album is put in a mixer which is previously heated at 45° C. The oils are added and the product is mixed for 10 minutes at a speed of 50 rotations per minute. Then the rest of the vaselinum album and the parafinum liquidum are added. Finally the mass is cooled down and packed in appropriate tubes.

EXAMPLE 13

Products for the Treatment of Animal Wounds

The substances used in the procedure for preparing the product are:

| | |
|---|---|
| medical powder | 92–94% |
| Origanum vulgaris oil | 4–6% |
| Thymus vulgaris oil | 0.5–1.5% |
| Mentha piperita oil | 0.5–1.5% |

20% of the medical powder is put in a vacuum mixer and mixed together with the oils which are mixed beforehand. The mixture is blended together for 10 minutes at a speed of 200 rotations per minute. Then the rest of the medical powder is added and mixed another 5 minutes at a speed of 150 rotations per minute. Finally the powder is packed in bags or bottles under pressure.

c) EXAMPLES CONCERNING THE ACTIVITY OF VETERINARY PHARMACEUTICAL MEDICAMENTS ACCORDING TO THE INVENTION

EXAMPLE 14

Introduction

Coccidiosis belongs to the most common acute diseases of the modern poultry upbringing. The disease is caused by monoxenous intercellular parasites from Eimeria species, from which pathogenecity depends the state of the disease and mortality level. Aiming for prevention and eradication of the coccidia today many chemotherapeutics are being used, but there appears to be a problem with the resistance of these parasites to them, especially if used inadequately and without changes. For this reason, the present invention provides immune protection of poultry (vaccines) by means of a preparation according to the invention composed of 5% by weight of Origanum vulgaris oil and 95% by weight of $CaCO_3$ and indicated below as "preparation A".

Materials and Methods of Work

The tests have been done on 75 chickens of the "Hybro" species. The chickens were grown on one mini-farm, with floor system and fed by standard concentrate "ad libidum". At the beginning of the test they have been separated in three groups of 25 animals each.

Group A: In 25 chickens one day old, preparation A has been added to the food as a prevention dose, which is 0.25 gr/kg of food for 7 days. After the 7th day, there was found an infection by oocysts of E. Tenella and E. Acervulima. After the infection the chickens were observed up to 28 days with regular examination of excrement. After the 28the day, the chickens were sacrificed and examined for its parasitology section, together with examination of the excrement.

Group B: Within this group of chickens, 25 chickens were given concentrate without coccistatics and test-preparation A. After the 7th day the infection by oocysts E. Tenella and E. Acervulina appeared. The same day preparation A was been mixed with the food of the animals in a concentration of 0.5 gr/kg of food. The chickens were fed by food mixed this way for seven days, and after this, were observed followed by regular parasitology examination started at the moment of detection of the infection. After the 28th day, the chickens were sacrificed and examined for its parasitology section, together with examination of the excrement.

Group C: In this group of 25 chickens, animals were fed 7 days with pure food, and after the 7th day there appeared an oocyst of E. Tenella and E. Acervulina infection. After clinical manifestation of the disease (7th day after infection) their food was mixed with preparation A, in a concentration of 0.5 gr/kg of food. The treatment lasted for 7 days while regular parasitology examinations were performed. 28 day old chickens were sacrificed and examined for its parasitology section, together with examination of the excrement.

The infection of the poultry has been obtained by tetrenic isolates of oocysts of E. Tenella and E. Acervulina, which after standard application and examination of the sporulation have been given to each individual chicken in doses of $1 \times 10^5$ oocysts. The examinations were performed by standard parasitology methods given by Johnson J. and Reid W. M., 1970, Anticoccidial drugs: lesion scorion technique in battery and floar pen experiments with chickens. Ex.Parasitol. 28, 30–36. The examinations were been done the first day after moving the chickens in, and after their infection in two day intervals during the complete test.

The Results of Test and Discussion

By examination done the first day after moving the poultry in, there has not been found a parasite infection in the animals. After the infection the examination was performed in two day intervals, in all three experiment groups. In groups A and B, coccidia was not detected in excrement. In group C the sixth day after infection the clinical symptoms of coccidiosis were detected (diarrhea, characteristic behaviour . . . ) as well as presence of oocysts of coccidia in the excrement. The second day after treatment, the diarrhea stopped but oocysts of coccidia were still found in the excrement. On the fourth day the number of oocysts significantly decreased and during next examination it dropped to a minimum. The clinical picture of the disease stopped after the fifth day of the treatment. No chickens died. After sacrifice of the chickens and parasitology section, together with examination of the excrement were performed by method of Johnson and Reid (1970), loc.cit. In groups A and B they have not been noticed while in group C they were not significantly important (level +1 according to this scale, never more than this).

Based on preliminary examination it can be concluded that the application of the preparation A can be used for coccidiosis of the poultry and have been efficient in preventive and therapeutic effect. Having in mind that the preparation contains 5% ethereal oil of *Origanum vulgaris* flower and leaf, which has a healing effect on the intestinal tract, this is probably the reason for the absence of changes in digestive tract of infected poultry clinically found before the application of the therapy. Within this group, the quick recovery was noticed and they have developed normally. It was noticed that poultry has normally taken the medicated food and that the strong smell of oregano has been absorbed in the food normally and therefore kept unnoticed. The powder is a better form for homogenization in concentration-form for the poultry. During the experiment, the poultry got all food ad libidum, and the micro-climate in the object moved between optimal limits for this kind of production and optimal space was provided for the animals.

Conclusion

Based on the experiment using preparation A for use in the prevention and eradication of coccidiosis in chickens we can conclude the following:

The preparation in the concentration of 0.25 gr/kg of food can be successfully used in prevention of this disease. The preparation should be used by adding it to the food within 7 days;

The preparation in the concentration of 0.50 gr/kg of food can be successfully used during the beginning and clinically manifested form of coccidiosis. Therapy should be applied for 7 days;

The preparation mixes easily with the food. The preparation smells strongly of oregano, but in the food it cannot be tasted. Chickens normally eat food with mixed preparation in it;

In treated chickens there were no side effects noticed as a consequence of the application of this preparation;

The preparation can be applied both for preventive or therapeutical use, and also for other diseases of poultry.

EXAMPLE 15

Introduction

As brought up in example 14, coccidiosis belongs to the most common parasitic diseases of poultry, for instance pheasants in intensive upbringing. The most common clinically manifested disease appears in pheasants aged 4–6 weeks, causing significant losses to this production. The coccidiosis prevention and therapy is analogous to the poultry production with the application of identical therapeutics. The problem of the resistance to it is present in this case as well. For these reasons the testing of the preventive and therapeutic effect of the preparation A (defined in example 14) was done and the results show significant efficiency of this preparation used in this test.

Materials and Methods of Work

The tests have been done of pheasants 3–6 weeks old, bearing in mind that coccidiosis in clinically manifested form appears in pheasants 4–6 weeks old. Based on dynamics of the production in the pheasant farm, every group of the birds counts approximately 2000 animals. The experiment has been performed on three groups.

Group A: On pheasants three weeks old, after parasitologic examination, in which no infection of cocci was found, preparation A has been added to the food. For prevention purposes, the preparation has been given in a concentration of 0.25 gr/kg of foods seven days in a row.

Group B: Within this group of pheasants, 24 days old, in obduction has been bound the beginning stage of the cocci infection. The estimation of the infection degree is being observed through the number of cocci and pathological changes in intestines. Determination of the causer-species is based on their morphological characteristics. After diagnosis the therapy doses of preparation A has been given in a concentration of 0.5 gr/kg of foods seven days in a row.

Group C: In this group the spring pheasants 4 weeks old, have clearly shown clinical symptoms of the disease. Characteristic behaviour of the birds and diarrhea were obvious in this group. *Hemoragical enteritis*, which mycosis corks in cecum, was observed. The death of the pheasants was within the limits of 50–60 birds daily. The therapy of preparation A has been applied in a concentration of 0.5 gr/kg of food.

Diagnosis of coccidiosis has been made by examining samples of excrement by standard parasitology methods. The smear of the mocous membrane has been done from the changed areas on intestines of the diseased pheasants. The estimation of extensivity and intensity of the infection has been done by counting oocysts of cocci, and based on the degree of pathological changes. Determination is based on morphological characteristics of the parasites by means of the Norton method (1981).

THE RESULTS OF TESTS AND DISCUSSION

Group A: Coccidiostatic effect of the preparation A has been completely successful. During observation of the animals for three weeks (ending 6th week) there were no cases of the presence of cocci. In obduction there were no parasite elements found (oocysts of cocci). Pheasants have developed normally, and the degree of mortality was below the technological range anticipated for this production (in average 1.1%).

Group B: Within this group of pheasants the beginning infection has been diagnosed, caused by *E. Duodenalis* and *E. Colchici*. The degree of the mortality was within technological limits, but the indication symptoms of the infection have been noticed. After 7-days of therapy the symptoms have completely disappeared and in obduction of dead and sacrificed animals there were no pathological changes in intestines and coccum, characteristic for coccidiosis. The examinations of the smear of mucous membrane have shown that the disease has not developed.

Group C: This group had present coccidiosis in clinical range followed by mortality of 2.5%. Infection has been caused by *E. Duodenalis* and *E. Colchici*. Therapy has been applied for 7 days. During the first three days the mortality has been significantly decreased, while after completed therapy coccidiosis has been eradicated completely. This has been approved by obduction and parasitology examination of the sacrificed and dead pheasants.

In both groups (B and C) where the infection has been noticed, after therapy there has been an important and significant improvement in condition and health of the birds. Following the development of these birds for the next several weeks, it has been noticed that vitality and development is within optimal range for this species. Estimation and following of the mortality of the birds has been made difficult by a worsening of the weather conditions (severe drop in temperature, heavy rains followed by wind), so that in the second week of the observation a slight increase of mortality has appeared, but based on section of dead animals (72 from B group, 61 from C group, and 60 from A group) and parasitology examination of dead animals and group excrement from experimental groups there was no coccidiosis found.

Conclusion

Based on experiments performed using preparation A for use of the prevention and eradication of coccisiosis in pheasant game birds in intensive upbringing we can conclude the following:

The preparation in the concentration of 0.25 gr/kg of food can be successfully used in prevention of this disease. The preparation should be used by adding it to the food within 7 days;

The preparation in the concentration of 0.50 gr/kg of food can be successfully used during the beginning and clinically manifested form of coccidiosis. Therapy should be applied for 7 days;

The preparation mixes easily with the food. The smell of the preparation is strong, specifically, of oregano, but in the food it cannot be tasted. Pheasants normally eat food with preparation mixed in it;

In treated pheasants there were no side effects noticed as a consequence of the application of this preparation;

The preparation can be applied both for preventive or therapeutical use, for the diseases of bacteridical or mycological ethiology of game birds. Based on shown coccidiostatic effect it may be applied for this use, like with application of other coccidiostatics (from third to eighth week of upbringing).

D) EXAMPLES CONCERNING THE SAFETY OF VETERINARY PHARMACEUTICAL MEDICAMENTS ACCORDING TO THE INVENTION

EXAMPLE 16

1. Introduction

In this example a study is carried out to get more information about the safety of pharmaceutical compositions comprising etheric oil of *Origanum vulgaris* (oregano oil) in broiler chicks. For this purpose two dietry levels were included in the trail: the normal recommended dose level of 250 ppm oregano oil and a dose level 10 times the recommended level (2,500 ppm of oregano oil). The latter dose level is generally used for testing the safety of products in order to apply for EU-registration referring to Council directive (COM C93 113) and Council decision (COM (93) 114). As a reference product, a commercially used antibiotic (virginiamycin; 20 ppm) was included in the trail. Birds were housed in battery cages for a period of 34 days. The criteria studied were weight gain, feed intake, feed conversion efficiency, water intake and general state of health.

2. Experimental Procedure 2.1. Experimental Groups

The following four experimental groups were involved in the trial:

| Group | Diet |
|-------|------|
| I | Basal diet (control diet without antibiotics) |
| II | Basal diet + 250 ppm oregano oil |
| III | Basal diet + 2,500 ppm oregano oil |
| IV | Basal diet + 20 ppm virginiamycin |

Each experimental group consisted of 90 thicks, six replicate cages each with 15 female birds.

2.2 Animals

A normal broiler cross ("Ross") was used. At the time of arrival at the institute, 460 one day old female birds were divided at random among 24 cages. During the pre-test period of 5 days all birds were fed a standard diet. At an age of 5 days 360 birds were selected and divided at random among the experimental groups according to body weight. The allocation was done in such a way as to obtain within each group two cages with 15 birds of an average body weight of 114 g, two with an average body weight of 107 g, and two with an average body weight of 102 g. After allocation the chickens were fed the experimental diets for 29 days (age period 5–34 days).

2.3 Variations

The birds were vaccinated for Newcastle disease (according to the spray method) at one and fourteen days.

2.4 Housing

The birds were housed in battery cages, situated in an artificially heated, ventilated and lighted broiler house. The broiler house involved 72 cages. The floor space of each cage was 0.98 square meters with wire floors. Each cage was provided with an automatic water supplier and a feed trough. Per cage, 15 birds were housed. The broiler house was illuminated 24 hours a day. During the experimental period, the light intensity was gradually reduced. The temperature in the broiler unit was gradually reduced from 28° C. during the first week to 23° C. during the last days of the experiment. The humidity in the broiler unit was approximately 55% during the experimental period.

2.5 Diets

For the experiment one batch of feedstuffs were used. The composition of the basic diet is presented in Table B. No coccidiostat was added to the diets.

The experimental diets were prepared at a feed mixing plant. The basal diet of the experimental groups was mixed as one batch for all groups. The experimental diets were then prepared by splitting up this batch into four batches to which the required amount of feed additives were added, and mixed. Next the diets were pelleted (2.5 mm) without the addition of steam. The pelleting temperature, measured after the pellets left the press, was approximately 54° C. The basal diet was analysed for the content of crude protein, Ca and P.

The diets were fed ad libitum. Water was also available ad libitum via an automatic device.

TABLE B

Composition of the basal diet (in %)

| Ingredient | |
|------------|---|
| Wheat | 35.00 |
| Corn | 10.00 |

TABLE B-continued

Composition of the basal diet (in %)

| | | |
|---|---|---|
| Soya oil | 3.10 | |
| Animal fat | 3.00 | |
| Tapioca | 3.94 | |
| Peas | 10.00 | |
| Soyabean meal (47.6% CP) | 15.00 | |
| Soyabean heattreated | 5.00 | |
| Sunflower meal | 5.00 | |
| Meat meal tankage (58% CP) | 5.00 | |
| Feathermeal (hydr. 82% CP) | 1.50 | |
| Vitamin-mineral mix* | 1.00 | |
| Limestone | 0.88 | |
| Monocalciumphosphate | 0.92 | |
| Salt | 0.26 | |
| L-lysine HCl | 0.20 | |
| Dl-methionine | 0.20 | |
| Crude protein | 22.3 | (21.9) |
| Dig. crude protein | 18.3 | |
| ME broilers (kcal/kg) | 2900 | |
| ME roosters (kcal/kg) | 3140 | |
| Crude fat | 9.4 | |
| Crude fibre | 3.6 | |
| Ash | 5.8 | |
| Calcium | 0.86 | (0.85) |
| Phosphorus | 0.71 | (0.73) |
| Available P | 0.45 | |
| Sodium | 0.16 | |
| Potassium | 0.85 | |
| Chloride | 0.28 | |
| Magnesium | 0.16 | |
| Linoleic acid | 3.0 | |

| Amino acids: | Total | AFD** |
|---|---|---|
| Lysine | 1.28 | 1.09 |
| Methionine | 0.54 | 0.48 |
| Meth. + Cyst. | 0.94 | 0.79 |
| Threonine | 0.82 | 0.67 |
| Tryptophan | 0.24 | 0.20 |
| Isoleucine | 0.90 | 0.76 |
| Leucine | 1.65 | 1.40 |
| Phenylalanine | 1.03 | 0.88 |
| Tyrosine | 0.70 | 0.58 |
| Valine | 1.06 | 0.87 |
| Arginine | 1.48 | 1.28 |
| Histidine | 0.51 | 0.43 |

*Supplied per kg diet: riboflavin, 4 mg; niacinamide. 40 mg; d-pantothenic acid, 12 mg; choline-chloride, 500 mg; cobalamin. 15 µg; D1-α-tocopheryl acetate. 15 mg; menadione 5 mg; retinyl-acetate, 3.44 mg; cholecalciferol, 50 µg; biotin, 0.1 mg; folic acid, 0.75 mg; $FeSO_4.7N_2O$, 300 mg; $MnO_2$, 100 mg; $CuSO_4.5H_2O$, 100 mg; $ZnSO_4.H_2O$, 150 mg; $Na_2SeO_3$, 0.15 mg; KI, 5 mg; $CoSO_4.7H_2O$,
1 mg: antioxidant (ethoxyquin), 100 mg; and 20 mg virginiamycin in phase 2.
**Apparent faecal digestible amino acids.
( ) Analysed contents 3. Criteria Studied
   Individual body weight after an experimental period of 14 and 29 days.
   Feed consumption for each replicate of 15 birds, at each time of weighing.
   Feed conversion efficiency, calculated as kg feed consumed/kg weight gain, at each time of weighing. The data for feed consumption and conversion efficiency were corrected for the estimated amount of feed consumed by birds which died during the experimental period.
   Water consumption and feed intake for each replicate of 15 birds, during one period of four days (24–28 days of age).
   Mortality rate, and general state of health.
4. Statistical Analysys
   The results for weight gain, feed conversion efficiency, feed intake and water consumption were analysed statistically. Results for weight gain, daily feed intake, and feed conversion efficiency are corrected for sex errors and 'outliers'. Differences among experimental groups were tested for significance by analysis of variance followed by the Least Significance Difference test (Snedecor and Cochran, 1980). The computer program SPSS/PC+ V5.0 (Norusis, 1992) was used to calculate the analysis of variance. All statements of significance are based on a probability of $P \leq 0.05$.

5. Conclusion

The results for weight gain, daily feed intake, and feed conversion efficiency at 14 and 29 days experimental period are presented in Tables C and D. Supplementation of either 250 or 2,500 ppm of organo oil to the diet had hardly any effect on eight gain and feed conversion efficiency after 14 and 29 days experimental period. Virginiamycin when added to the diet tended to improve weight gain and feed conversion efficiency after 14 days experimental period, whereas hardly any effect on broiler performance was obtained after 29 days experimental period. The results for water intake and water/feed ratio are presented in Table E. Inclusion of either 250 and 2,500 ppm of oregano oil, or 20 ppm virginiamycin in the diet had hardly any effect of daily water intake and water/feed ratio.

Mortality rate was low, 1.4% (=5 animals), with no appreciable differences among the treatment groups. In addition, no abnormalities regarding the health status were observed during the trial. The low mortality rate obtained during the present trial indicates that the animals were in good health condition. This good health condition of the birds in the present study may explain the fact that hardly any effect of virginiamycin on broiler performance was observed, whereas normally an improvement in feed conversion efficiency is observed. Based on the results of the present study it can be concluded that oregano oil has no negative or detrimental effect on performance of healthy broiler chicks when supplemented 10 times the recommended level.

TABLE C

Results for body weight gain, daily feed intake, and feed conversion efficiency of broiler chicks after 14 days experimental period (5–19 days of age).

| | | Weight gain | | Feed intake | | Feed gain | |
|---|---|---|---|---|---|---|---|
| Group | Addition of | (g) | % | (g/d) | % | ratio | % |
| I | — | 585 | 100 | 60.6 | 100 | 1.450 | 100 |
| II | 250 ppm Origanum oil | 577 | 98.6 | 59.4 | 98.0 | 1.441 | 99.4 |
| III | 2,500 ppm Origanum oil | 582 | 99.5 | 60.3 | 99.6 | 1.452 | 100.1 |
| IV | 20 ppm virginiamycin | 592 | 101.1 | 60.5 | 99.8 | 1.431 | 98.7 |
| LSD (P = 0.05) | | 14 | | 1.0 | | 0.021 | |

TABLE D

Results for body weight gain, daily feed intake, and feed conversion efficiency of broiler chicks after 29 days experimental period (5–34 days of age).

| Group | Addition of | Weight gain (g) | % | Feed intake (g/d) | % | Feed gain ratio | % |
|---|---|---|---|---|---|---|---|
| I | — | 1590 | 100 | 93.7 | 100 | 1.710 | 100 |
| II | 250 ppm Origanum oil | 1571 | 98.8 | 92.2 | 98.3 | 1.702 | 99.5 |
| III | 2,500 ppm Origanum oil | 1593 | 100.2 | 94.0 | 100.3 | 1.711 | 100.1 |
| IV | 20 ppm virginiamycin | 1606 | 100.3 | 93.4 | 99.6 | 1.697 | 993 |
| LSD (P = 0.05) | | 38 | | 1.9 | | 0.024 | |

TABLE E

Results for water consumption and water feed ratio of broiler chicks during one period of four days (24–28 days of age).

| Group | Addition of | Daily water intake (g/d) | % | Water/feed ratio | % |
|---|---|---|---|---|---|
| I | — | 291 | 100 | 2.06 | 100 |
| II | 250 ppm Origanum oil | 295 | 101.3 | 2.07 | 100.7 |
| III | 2,500 ppm Origanum oil | 295 | 100.3 | 2.09 | 101.4 |
| IV | 20 ppm virginiamycin | 290 | 99.6 | 2.08 | 101.2 |
| LSD (P = 0.05) | | 13.2 | | 0.07 | |

What is claimed is:

1. A method of reducing the incidence of or treating a gastrointestinal infection in birds or mammals comprising orally administering to said birds or mammals an effective amount of a pharmaceutical composition, wherein the composition consists essentially of an active agent and a pharmaceutically acceptable carrier, wherein the active agent is an oil consisting essentially of a combination of thymol and carvacrol, said oil being extracted from *Origanum vulgaris* plants, wherein the oil is 1–15% by weight of the total weight of the pharmaceutical composition.

2. The method of claim 1, wherein the oil is 4–10% by weight of the total weight of the pharmaceutical composition.

3. The method of claim 1, wherein the pharmaceutical carrier is selected from the group consisting of lactose, honey, laurel, vaseline, paraffin, and calcium carbonate.

4. The method of claim 1, wherein the birds are poultry.

5. The method of claim 4, wherein the method is to treat a gastrointestinal infection, wherein said gastrointestinal infection is coccidiosis.

6. The method of claim 4, wherein the method is to reduce the incidence of a gastrointestinal infection, wherein said gastrointestinal infection is coccidiosis.

7. A pharmaceutical composition for oral administration in a veterinary application, consisting essentially of a pharmaceutically acceptable carrier, *Origanum vulgaris* oil 3–5% by weight of the total pharmaceutical composition, *Thymus vulgaris* oil 1–3% by weight of the total pharmaceutical composition, and *Mentha piperita* oil 0.5–1.5% by weight of the total pharmaceutical composition.

8. A method of treating coccidiosis in poultry, comprising the step of administering an effective amount of the composition of claim 7.

9. A method of reducing the incidence of coccidiosis in poultry comprising orally administering an effective amount of a pharmaceutical composition to said poultry, wherein the composition consists essentially of an active agent and a pharmaceutically acceptable carrier, wherein the active agent is an oil consisting essentially of a combination of thymol and carvacrol, said oil being extracted from *Origanum vulgaris* plants.

10. The method of claim 9, wherein the oil is 4–10% by weight of the total weight of the pharmaceutical composition.

\* \* \* \* \*